April 8, 1975 T. YUGE Plant Pat. 3,702
AZALEA PLANT
Filed May 3, 1974
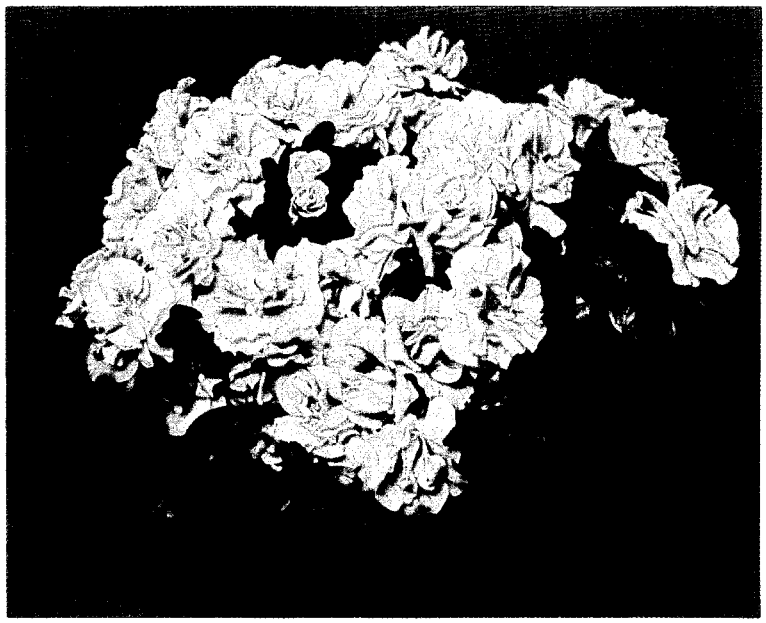
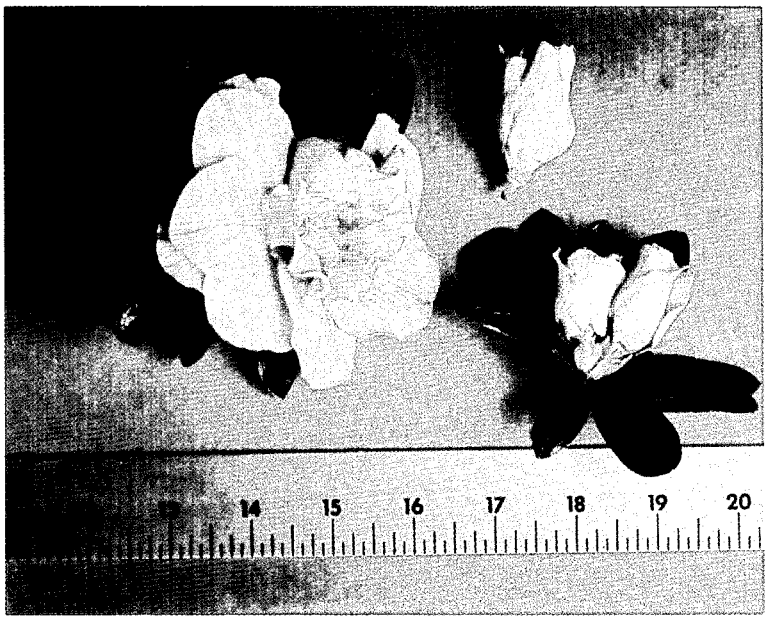

United States Patent

Plant Pat. 3,702

Patented Apr. 8, 1975

3,702

AZALEA PLANT

Takeo Yuge, Altadena, Calif., assignor to Geo. J. Ball, Inc., Chicago, Ill.

Filed May 3, 1974, Ser. No. 466,739

Int. Cl. A01h 5/00

U.S. Cl. Plt.—56 1 Claim

ABSTRACT OF THE DISCLOSURE

A new and improved variety of azalea plant for pot forcing characterized by its abundant production of large flowers, distinguished by an attractive pink coloring, by its vigorous, upright and spreading growth habit, and by its abundant production of foliage.

BACKGROUND OF THE NEW PLANT

My new variety of azalea plant originated in 1970 as a seedling of Jane Haerens (unpatented) × Red Hot (P.P. 3,155) developed in the course of a breeding program carried on by me at Altadena, Calif., with the purpose of producing new and improved azalea varieties for the commercial trades. This particular plant was selected by me for propagation and test because of its abundant production of large blossoms of a very attractive color. My subsequent asexual propagation of this plant, by means of cuttings, at Altadena, Calif., has demonstrated that it has the additional advantage of being a vigorous grower with abundant foliage and sturdy, spreading branches. Propagation of this new plant through successive generations shows that all of the desirable characteristics of the plant hold true and appear to be permanently fixed.

Propagation of this new azalea variety is now being carried on at Salem, Oreg., at Woodburn, Oreg., and at San Fernando, Calif.

DESCRIPTION OF THE DRAWING

This new variety of azalea plant is illustrated by the accompanying photographic drawing which shows a potted plant in full bloom in one view and in another view shows a close-up of a fully opened flower and several buds, the colors shown being as nearly true as can reasonably be had by conventional photographic procedures. The true colors are shown by the painted color swatches A and B affixed to the drawing, the color A being that of the central base portion of the flower petal and the color B being the principal color of the main body of the petal.

DESCRIPTION OF THE NEW PLANT

The following is a detailed description of my new variety of azalea plant, with the color designations according to the Robert F. Wilson Horticultural Colour Chart published by the Royal Horticultural Society of London, England, in collaboration with the British Colour Council.

The plant

Origin: Seedling.
Parentage:
*Seed parent.*—Jane Haerens (unpatented).
*Pollen parent.*—Red Hot (Plant Pat. 3,155).
Classification:
*Botanic.*—Rhododendron.
*Commercial.*—Hyrid azalea.
Form: Bush, as a potted plant.
Height: Medium.
Growth: Vigorous and upright, with sturdy, limber and spreading branches.
Foliage: Quantity—abundant.
*Leaf.*—Size; Variable, up to 2 inches long and 1 or more inches in width. Shape: Obovate to oblanceolate. Texture: Leathery and hirsute. Aspect: Glossy. Ribs and veins: Alternate pinnate venation. Color: Upper side—Ivy Green 0001060/1. Under side—Spinach Green 0960/2.
*Petioles.*—Length—¼ to ¾ inches.

The bud

Size: Fairly large—½ to 1 inch wide and 1 to 1¾ inches long.
Form: Urn shaped.
Opening rate: Slow.
*Color.*—When sepals first divide—Magenta 27/1. When petals begin to unfurl—Tyrian Rose 24/2.
*Sepals.*—Upstanding and pointed with outwardly curled tip. Color: Inside—Pod Green 061/1, Scheeles Green 860 at curled-out tip. Outside—Pod Green 061.
*Calyx.*—Size—Small. Shape: 5-lobed star-shaped. Aspect: Hairy.
Peduncle: Erect—¼ to ½ inch in length.
*Aspect.*—Hairy.
*Color.*—Pod Green 061.

The flower

Blooming habit: Recurrent. This plant blooms profusely, once about midseason of spring, and has a tendency to give few blooms in fall.
Size: Very large.
*Diameter.*—2¾ to 4 inches.
*Depth.*—1 to 1¾ inches.
Borne: In cluster.
Shape: Urceolate at first opening, becoming a broad funnel-shape as the petals unfold and having a high center, due to profusion and ruffling of petaloids, as the blossom matures.
Petalage: Number of petals—8 to 12 full-sized petals with 6 to 10 petaloids or small petals of varying size.
*Arrangement.*—Double, appearing to be hose-in-hose but actually petals are fused together for the first ½ inch of length.
*Form.*—Ovate base, with broad obtuse apex and with entire and slightly undulate margins.
*Color.*—Outer Petal—Tyrian Rose 24/1 at base shading into 24/2 toward petal margin and having a slight penciling of Rose Bengal 25/1 and some blotching with Spirea Red 025. Inside petal—Same as outer petal. Reverse side—Rose Bengal 25/1.
*Texture.*—Soft.
*Aspect.*—Satiny.
Peduncle: Sturdy, upright and tomentose, ¼ to ½ inch long.
*Color.*—Pod Green 061. At full bloom one side of peduncle is shaded with Claret Rose 021/1.
Discoloration after full bloom: Slight.
Persistence: Petals hang on and dry.
Fragrance: None.
Lasting quality: Very good on plant. Not used for cut flowers.

Reproductive Organs

Stamens:
*Anthers.*—1 to 4 in number.
*Filaments.*—½ to 1 inch long and partially petalody, sometimes with one or more fused to petals up to the anther.
*Pollen.*—Color—Black tip on stamen, sometimes with a very small amount of white pollen.
Pistils: Number—One.
*Styles.*—Length—¾ to 1¼ inch. Color—Rose Red 724/2.

*Stigma.*—Color—Mature flower—China Rose 024/2.
Partially open flower—Sap Green 62/2.

Ovaries: Superior, heavily covered with silver-white hairs.

This new variety of azalea plant has particularly advantageous characteristics for the commercial trade because of its vigorous and uprightly spreading growth habit and its profuse production of very large, delicate pink flowers crowning an abundant growth of glossy dark green foliage. This plant is especially adapted for pot forcing and its blooms have excellent keeping qualities.

I claim:

1. A new and distinctive variety of azalea plant substantially as herein shown and described, characterizes by its profuse production of very large delicate pink blossoms appearing as a mass above an upright and spreading growth of abundant foliage.

No references cited.

ROBERT E. BAGWILL Primary Examiner